US006867420B2

(12) United States Patent
Mathies et al.

(10) Patent No.: US 6,867,420 B2
(45) Date of Patent: Mar. 15, 2005

(54) SOLID-STATE DETECTOR AND OPTICAL SYSTEM FOR MICROCHIP ANALYZERS

(75) Inventors: Richard A. Mathies, Moraga, CA (US); Toshihiro Kamei, Emeryville, CA (US); James R. Scherer, Richmond, CA (US); Robert A. Street, Palo Alto, CA (US)

(73) Assignee: The Regents of the University of California, Oakland, CA (US)

( * ) Notice: Subject to any disclaimer, the term of this patent is extended or adjusted under 35 U.S.C. 154(b) by 217 days.

(21) Appl. No.: 10/269,138

(22) Filed: Oct. 10, 2002

(65) Prior Publication Data

US 2003/0222223 A1 Dec. 4, 2003

Related U.S. Application Data (60) Provisional application No. 60/385,770, filed on Jun. 3, 2002.

(51) Int. Cl.[7] .................................................. G01J 1/58
(52) U.S. Cl. .............................. 250/458.1; 250/462.1; 438/65; 438/57
(58) Field of Search .......................... 250/458.1, 462.1; 438/65, 57

(56) References Cited

U.S. PATENT DOCUMENTS

| 4,755,667 A | | 7/1988 | Marsoner et al. | |
|---|---|---|---|---|
| 4,937,454 A | * | 6/1990 | Itoh et al. ............... | 250/370.11 |
| 5,039,490 A | | 8/1991 | Marsoner et al. | |
| 5,439,647 A | | 8/1995 | Saini | |
| 5,933,233 A | | 8/1999 | Günther | |
| 6,040,591 A | | 3/2000 | Otsuka | |
| 6,133,954 A | | 10/2000 | Jie et al. | |
| 6,395,576 B1 | | 5/2002 | Chang et al. | |
| 6,448,064 B1 | * | 9/2002 | Vo-Dinh et al. ......... | 435/287.2 |

FOREIGN PATENT DOCUMENTS

| DE | 41 22 925 A1 | 1/1993 |
|---|---|---|
| WO | US99/19501 | 3/2000 |
| WO | US03/17504 | 6/2003 |

OTHER PUBLICATIONS

Thrush et al., AIntegrated Bio–Fluorescence Sensor,@ *Stanford Photonics Research Center conference*, Sep. 2001.

Thrush et al., Integrated Semiconductor Fluorescent Detection System for Biochip and Biomedical Applications,@ *SPIE*, vol. 4626, Jan. 2002.

Mizukami, Y., et al. AA Novel Microchip for Capillary Electrophoresis with Acrylic Micochannel Fabrication on Photosensor Array,@ *Sensors and Actuators* B 81 (2002) 202–209.

Krishnan, M. et al., AA Novel Strategy for the Design of Multiple Reaction Systems for Genetic Analysis,@ *Sensors and Actuators* A 95 (2002) 250–258.

Street, R.A., et al., AAmorphous Silicon Arrays Develop a Medical Image,@ *IEEE* Circuits and Devices (Jul. 1993) 38–42.

Webster, J.R., et al., Monolithic Capillary Electrophoresis Device with Integrated Fluorescence Detector,@ *Analytical Chemistry*, vol. 73, No. 7, Apr. 1, 2001.

(List continued on next page.)

*Primary Examiner*—David Porta
*Assistant Examiner*—Christine Sung
(74) *Attorney, Agent, or Firm*—Dorsey & Whitney LLP (57) ABSTRACT

A miniaturized optical excitation and detector system is described for detecting fluorescently labeled analytes in electrophoretic microchips and microarrays. The system uses miniature integrated components, light collection, optical fluorescence filtering, and an amorphous a-Si:H detector for detection. The collection of light is accomplished with proximity gathering and/or a micro-lens system. Optical filtering is accomplished by integrated optical filters. Detection is accomplished utilizing a-Si:H detectors.

29 Claims, 8 Drawing Sheets

OTHER PUBLICATIONS

Ma, E., et al., AMicrolens Arrays with Integrated Thin Film Power Monitors,@ *IEEE* 2001 Electronic Components and Technology Conference.

Burke, David T., et al., Microfabrication Technologies for Integrated Nucleic Acid Analysis,@ *Genome Research*, Cold Spring Harbon Laboratory Press, ISSN 1054–9803 (1997).

Burns, Mark A., An Integrated Nanoliter DNA Analysis Device,@ *Science@* Oct. 16, 1998, vol. 282 484–487.

Thrush et al., "Integrated Semiconductor Fluorescent Detection System for Biochip and Biomedical Applications",@ *SPIE*, vol. 4626, Jan. 2002, pp 374–379.

Integration of lasers, detectors and processing electronics in a highly compact and functional cube about $1cm^3$ in size@ BIOMEMS 2001, May 17–18, 2001, Radisson Inn, Sunnyvale, CA.

* cited by examiner

FIG_1

FIG_2

FIG_3

FIG_4

FIG_5

FIG_6

FIG_7

FIG_8

FIG_9

FIG_10

FIG_11

FIG_12

FIG_13

FIG_14

FIG_15

SOLID-STATE DETECTOR AND OPTICAL SYSTEM FOR MICROCHIP ANALYZERS

RELATED APPLICATIONS

This application claims priority to U.S. Provisional Application Ser. No. 60/385,770 filed Jun. 3, 2002.

GOVERNMENT SUPPORT

This invention was made with Government support under Grant No. FG03-91ER61125 awarded by the Department of Energy. The Government has certain rights to this invention.

BRIEF DESCRIPTIONS OF THE INVENTION

This invention relates generally to a solid state detector and optical system for detecting fluorescently labeled analytes in microchips and microarrays, and more particularly to a system employing a-Si:H photodetectors, filters and microlenses.

BACKGROUND

There is tremendous demand for chemical and bioanalytical devices that enable high throughput and performance assays in small point-of-care or point-of-analysis devices. Ultimately, these devices should be portable and disposable. To this end, microfabricated capillary array electrophoresis (µCAE) devices are a promising candidate. µCAE can be used to carry out a wide variety of analyses such as amino acid analysis, protein and small analyte analysis, DNA fragment sizing and DNA sequencing with much greater efficiency than conventional methods (Micro Total Analysis Systems 2001 Ed. Ramsey & van den Berg, Kluwer Academic Press Dordrecht, 2001). Capillary electrophoresis (CE) measurements have been multiplexed to perform massively parallel, high-throughput genotyping on from 96 to 384—lane µCAE devices.

Most µCAE devices, however, still use conventional off-chip laser-induced fluorescence detection, including photomultiplier tubes, CCDs, optical filters, lenses, lasers, and so forth. Such a bulky detection system inhibits many potential point-of-analysis benefits possible with µCAE devices. In order to make a portable device, miniaturized excitation and detection systems must be developed. One means of accomplishing this is to use electrochemical detection, as addressed by Woolley et al. in Analytical Chemistry, 70, 684–698 (1998). On-chip electrochemical detection has attractive features such as a simple structure and ease of manufacturing, however, electrochemical detection has limited detection sensitivity compared to fluorescence. Furthermore, it is difficult to perform multiplexed assays such as DNA sequencing or certain protocols for single nucleotide polymorphisms (SNP) detection.

Fluorescent detection is very sensitive, especially when combined with laser excitation. Multiplexed detection is also feasible and routinely used in modern DNA sequencers. Therefore, it is beneficial to maintain fluorescence detection for bioanalytical chips and devise ways to miniaturize and integrate the excitation and detection system. Mastrangelo and co-workers have presented a system where they have fabricated silicon (Si) photodiodes directly on an Si wafer containing the microfluidic system (M. A. Burns et al., Science, 282, 484 (1998), J. R. Webster et al., Analytical Chemistry, 73, 1622 (2001)). This monolithic fabrication complicates electrophoresis because of the conductivity of Si substrates. In this case, the fluidic CE channel had to be electrically insulated from the silicon substrate by depositing material such as parylene-C, SiN, or $SiO_2$ on the channel. The costs associated with the fabrication of single crystalline silicon systems are relatively high because of the high cost of single crystalline Si wafers and the multiple process steps that are required. Mariella has presented a portable DNA analyzer which performs the real-time polymerase-chain-reaction assays based on fluorescence detection using a homogenous TAQ-man assay, but his system is not designed for microfluidic channels and employs large microliter (µL to mL) volume of samples (Mariella, Jr., JALA, 6, 54 (2001)).

SUMMARY AND OBJECTS OF THE INVENTION

In the present invention, hydrogenated amorphous silicon (a-Si:H) photodiodes are used in a miniaturized integrated fluorescence detector system for µCAE devices. Such a-Si:H photodiodes can be deposited at a very low temperature (~200° C.) by plasma assisted decomposition of $SiH_4$ gas or a mixture of $SiH_4$ and $H_2$ gas. The entire low-temperature process allows for direct fabrication of a-Si:H photodiodes on inexpensive substrates such as glass or flexible plastic film (Ichikawa et al., J. Non-Cryst. Solids, 198–200, 1081 (1996)). In addition, a-Si:H has many advantages in manufacturing, patterning, and low production cost, demonstrated by its implementation in thin film transistors (TFT) for active matrix liquid crystal displays and in image sensor arrays which combine a-Si:H photodiodes with a TFT readout (R. A. Street et al., MRS Symp. Prac: 192, 441 (1990) and R. A. Street and L. E. Antonuk, IEEE Circuit and Devices, Vol. 9, No. 4, 38–42 (July 1993)).

It is an object of the present invention to provide an integrated detector and optical system for fluorescent detection in microchip analyzers.

It is another object of the present invention to provide an integrated detector system employing a-Si:H photodetectors, optical filters and microlenses for fluorescent detection in capillary electrophoresis devices.

It is a further object of the present invention to provide an easily fabricated and inexpensive integrated detector and optical system for fluorescent detection in microchip analyzers.

The foregoing and other objects of the invention are achieved by a detector system which employs integrated a-Si:H photodiodes and optical filters for detecting light emitted by fluorophores. More particularly, the invention relates to the use of integrated a-Si:H detectors, optical filters and lenses forming an integrated system for fluorescent detection of labeled components separated in electrophoresis channels.

BRIEF DESCRIPTION OF THE DRAWINGS

The foregoing and other objects and features of the invention will be more clearly understood with reference to the following description when read in conjunction with the accompanying drawings in which.

DESCRIPTION OF PREFERRED EMBODIMENT

Figure 1:
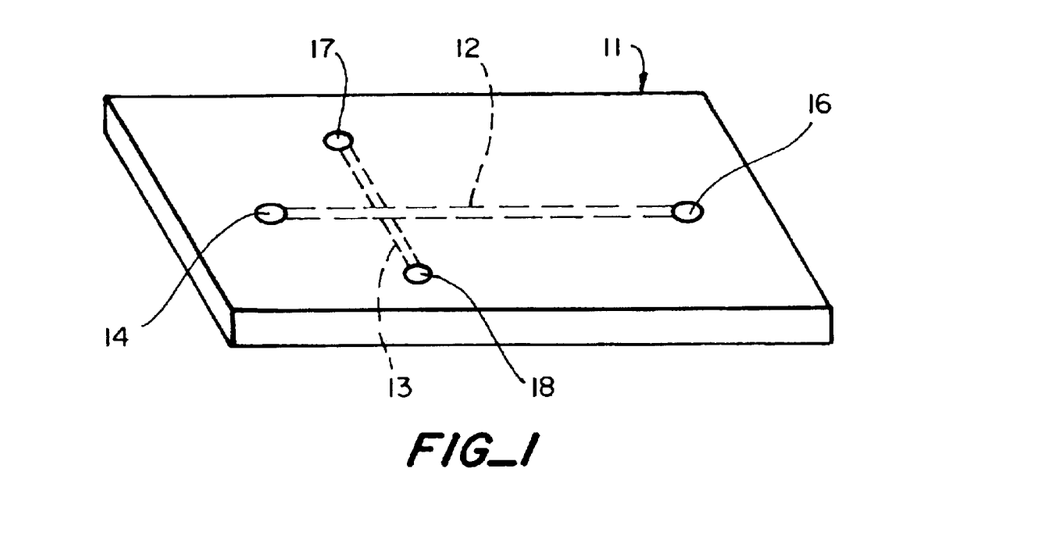
FIG. 1 is a representation of a microfabricated capillary electrophoresis device.

FIG. 1 schematically illustrates a capillary electrophoresis chip 11 with separation channel 12 and cross injection channel 13. Capillary electrophoresis separating voltage is applied between the cathode 14 and anode 16. The analyte or sample is introduced at well 17 for migration across the injection channel when a voltage is applied between the wells 17 and 18. In accordance with well-known techniques, the sample is labeled with a suitable fluorophore so that when a labeled component is illuminated with light at one frequency it fluoresces and emits light at a different frequency. The sample is separated by electrophoresis as it travels along the channel and when the labeled components reach a detection region where they are illuminated, they fluoresce and the emitted light is detected to identify the labeled component as a function of its arrival time at the detector.

Figure 2:
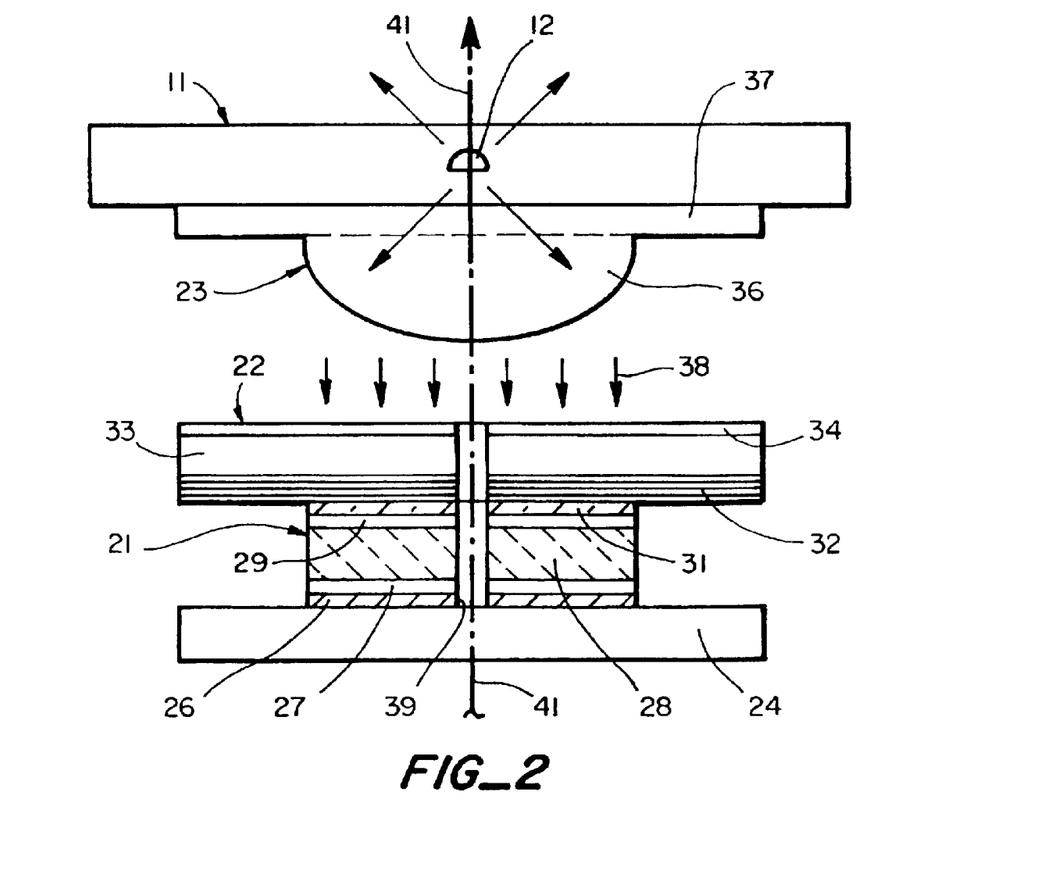
FIG. 2 shows a photodetector, filter and lens in accordance with one embodiment of the present invention coupled to an electrophoresis device.

FIG. 2 shows an integrated a-Si:H photodiode detector 21, an optical system including an optical interference filter 22, and lens 23. Plasma assisted decomposition of $SiH_4$ gas, or a mixture of $SiH_4$ and $H_2$ gas, is used to fabricate the photodiode detector at low temperatures. The process allows for fabrication of a-Si:H photodiodes on inexpensive substrates 24 such as glass or plastic. The photodiodes are fabricated by first forming a metal electrode 26 by vapor deposition or sputtering of a metal layer, such as chromium or aluminum. Then, in succession, an n-type a-Si:H layer 27 is deposited followed by an intrinsic a-Si:H layer 28 and a p-type a-Si:H layer 29. The second contact comprises a deposited transparent conductive oxide layer 31, such as ITO, $SnO_2$ or Al or Ga-doped ZnO. The order of the p-type and n-type layers can be reversed. However, light injection into the p-layer provides higher photocurrent due to the low mobility of holes as compared to electrons. The optical interference filter 22 is formed by depositing layers 32 of material such as $TiO/SiO_2/SiN$, etc. of selected thickness on a quartz or other glass plate 33. The fabrication of interference filters is well-known in the art and is not further described. An anti-reflection coating 34 is preferably applied to the other surface of the quartz plate to increase the collection efficiency. A microlens 36 completes the detection and optical system. The microlens 36 can be fabricated by injection molding the microlens 36 and bonding it to a plate 37 which may form part of the μCAE device or, alternatively, the lens 36 and support 37 could be fabricated as one piece by injection molding. The lens and support can be attached to the photodetector and filter to form an integrated assembly. The microlens 36 may for example be a convex lens, an aspheric lens, a half-ball lens, a graded refractive index lens or a diffractive lens. The lens serves to collimate the fluorescent light emitted by fluorophores at the microchannel 12 as indicated by arrows 38. This enhances gathering of the desired fluorescence and attenuation of the laser excitation light because the optical density of the interference filter is dependent on the incident angle of light. When the solid angle for collecting fluorescence is large, reflection at the interface between microplate and lens can be eliminated by using an index matching fluid.

In accordance with the preferred embodiment of the invention, photodiode 21 and optical filter 22 include a pinhole 39. The excitation light beam 41 is projected through the glass substrate 24, the pinhole 39 and lens 36 to the microchannel 12. An anti-reflection coating (not shown) can be applied to the glass substrate to increase the efficiency of transmission of the light beam through the glass substrate and to reduce scattered light. The light beam may be generated by a semiconductor laser (edge-emitting type or vertical cavity type) or a small conventional laser or LED. The metal contact or electrode 26 is of sufficient thickness to act as an aperture which defines the size of the transmitted beam. The vertical laser excitation keeps laser light from directly impinging on the optical filter and the detector.

The glass substrate 24 and glass plate 37 can be supported in spaced relationship by a spacer (not shown) and the filter assembly 32, 33 and 34 attached to the photodiode 21. This combination provides a detector and optical assembly which can be used to read μCAE devices 11 by placing them one at a time in cooperative relationship therewith. The fluorescence emitted by a fluorophore excited by the light beam 41 is collimated by the lens and transmitted to the photodiode 21 through the filter 22 which transmits light at the fluorescent wavelength and adsorbs or reflects light at the excitation wavelength.

Figure 3:
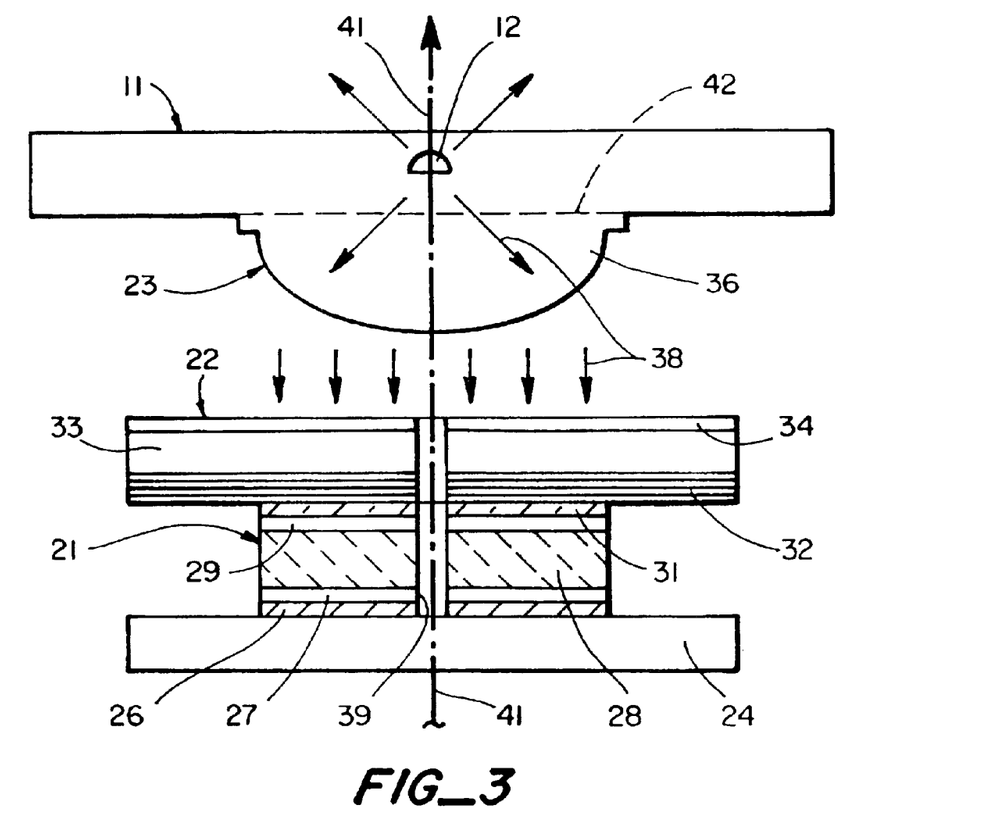
FIG. 3 shows a photodetector, filter and lens with the lens being a part of the electrophoresis device.

FIG. 3 shows a μCAE device which is fabricated by molding the lens directly in the μCAE device as indicated by dotted line 42. Other reference numbers refer to parts like those of FIG. 3.

Figure 4:
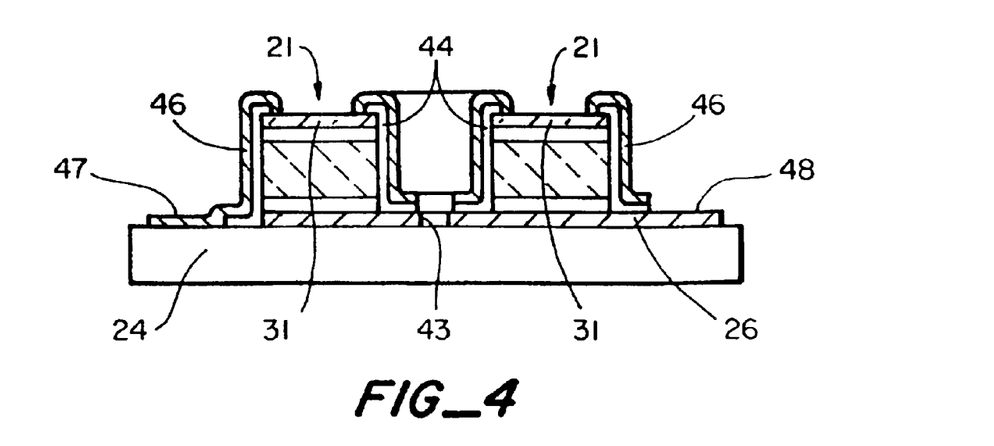
FIG. 4 is a detailed view of the photodetector used in the present invention.
Figure 5:
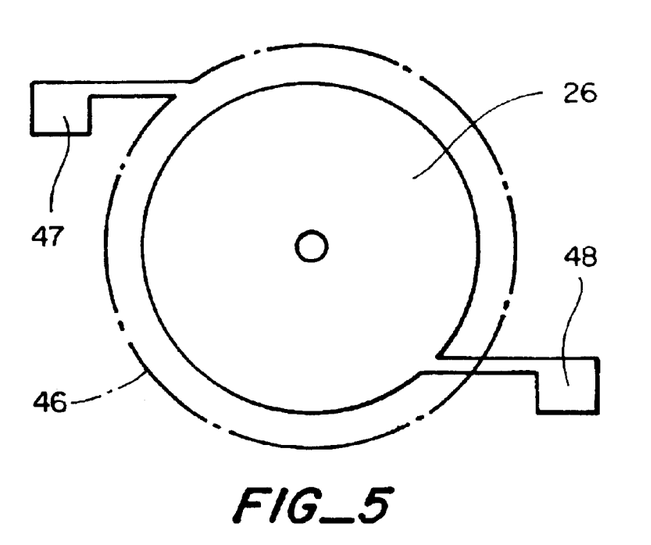
FIG. 5 is a top plan view of the photodetector of FIG. 4.

To reduce the possibility of introducing scattered light from the side, it is important to minimize the distance between the optical filter and the a-Si:H detector. Hence, the filter layer is underneath the quartz or transparent plate 33 and the a-Si:H detector is put upward on glass substrate 24. To minimize the effect of laser scattered light, a metal light shield can be formed inside the aperture or pinhole of the a-Si:H detector. Referring to FIG. 4, the photodiode 21 is formed with the bottom electrode 26 having a small aperture 43. An insulating layer 44 such as SiN or an oxide is formed on the outer surfaces of the photodiode 21 and the surface of the pinhole 39. This is followed by a metal layer 46 such as aluminum which connects to the top electrode 31. The metal electrode also serves to block scattered light. FIG. 5 shows contact pads 47 and 48 for the top and bottom electrodes.

It should be noted that laser beam path could be reversed. There may be an advantage in illumination of the CE channel from above. The transmitted beam would then pass through the hole in the detector. However, it might be more difficult to protect the a-Si:H detectors from the high intensify of the laser beam and scattering from that beam. Besides, strong forward scattered light may adversely affect the filter, especially during the alignment of the optics.

Figure 6:
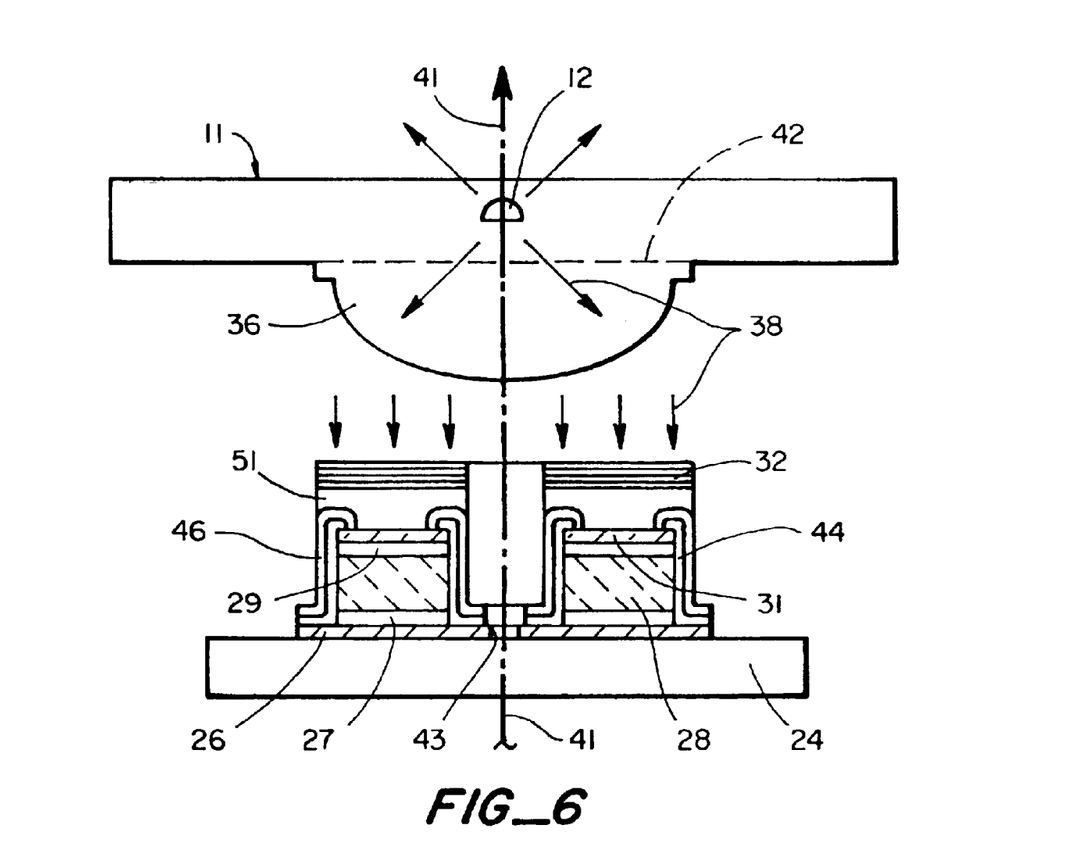
FIG. 6 shows a detection system in which the filter is integrated with the photodetector.

Shown in FIG. 6 is the monolithic integration of the optical filter and a-Si:H detector based on the device structure of FIGS. 2–5, where like reference numerals have been applied to like parts. The a-Si:H detector is tolerant of the coating temperature of some types of optical filters such as ZnS/YF$_3$. The fabrication process would proceed as follows. First, a-Si:H photodiodes are deposited on the glass substrate, followed by the deposition of diffusion barrier layer 51 such as silicon oxide or silicon nitride. Second, the optical interference filter is coated on it. Before coating the filter, planarization of diffusion barrier oxide layer 51 is accomplished by chemical mechanical polishing (CMP), which is important for the quality of the optical interference filter. It is also noted that metal sidewall protection of photodetector can be extended to the top of the optical interference filter, so that further reduction of laser light scattering would be realized.

Figure 7:
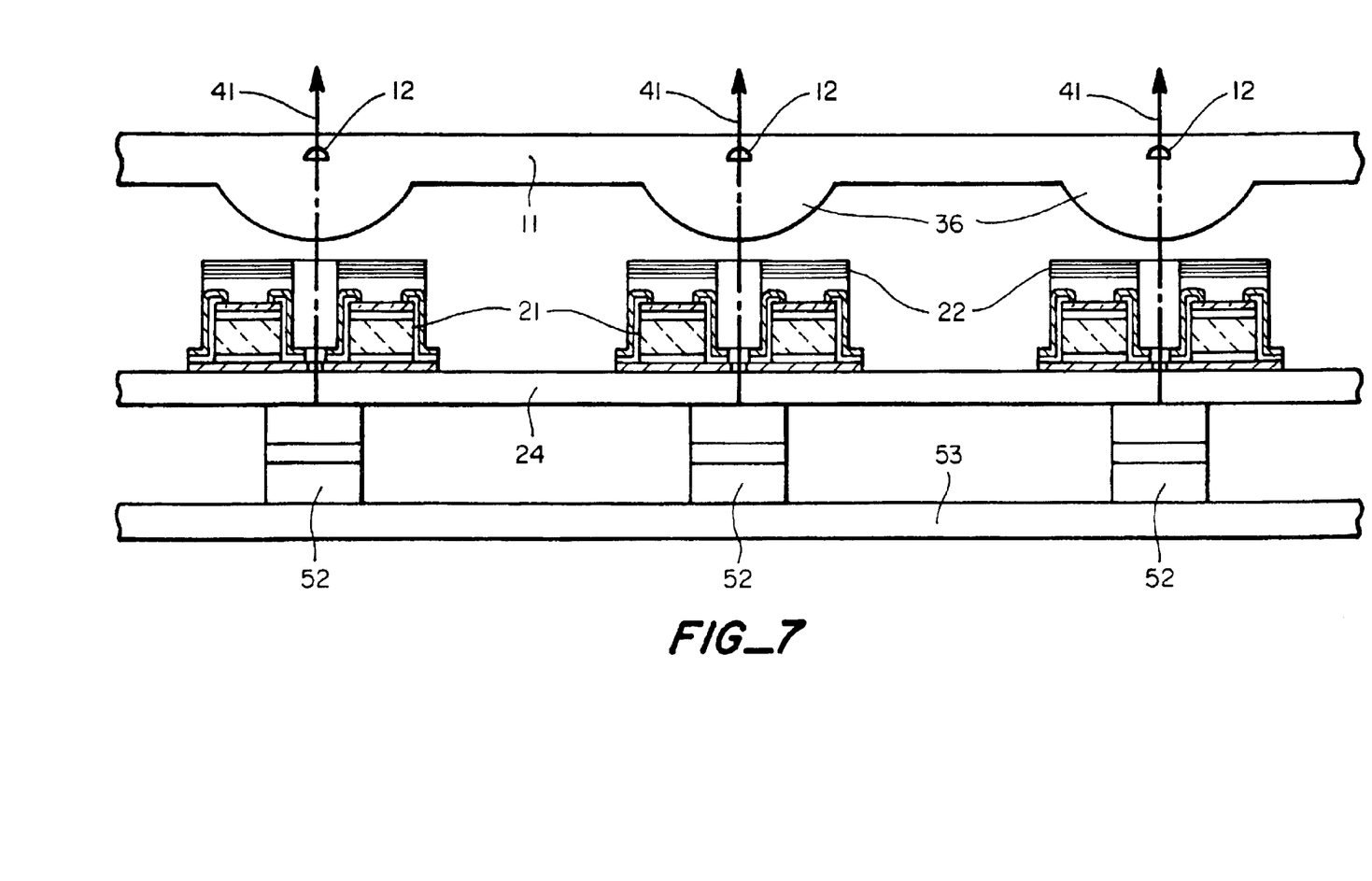
FIG. 7 shows a system including VCSELs coupled to an array of integrated filters and photodetectors of FIG. 6.

An array of detectors, filters and lens can be used to detect fluorescent light from spaced electrophoresis channels 12. FIG. 7 shows an array of the monolithically integrated optical filter and detectors coupled to μCAE channels 12. An array of vertical cavity surface emitting lasers 52 (VCSEL) is coupled to the detector and filter to provide the excitation light. The array of VCSEL can be fabricated on wafer 53 and are inherently scalable, because each laser diode is patterned by photolithography. The a-Si:H detectors 21 and filters 22 are monolithically integrated with VCSEL array. Since the very low deposition temperature of a-Si:H detectors and optical filter (<200° C.) suppresses the interdiffusion of elements between a-Si:H and VCSEL (normally made of compound semiconductor such as GaAs alloy or GaN alloy), the monolithic integration does not adversely affect the performance of VCSEL and a-Si:H detector. In this embodiment, the lens 36 is formed integral with the μCAE 11 as for example by molding, although it could also be a discrete component unit or it could be integrated with the detector array. It should also be noted that one could alternatively use a single laser with radial scanner or glavoscanner, a single laser with several beamsplitters, or a single laser coupled to a fiber optic array to direct laser excitation to each sampling point. It is apparent that the array may be two-dimensional so that it senses fluorescent light at locations along each of the multiple channels. With a two-dimensional configuration, fluorescent light from a conventional DNA or protein array could be detected. The lens, filter, detector and light source can be integrated into a single unit. It can then be used to sequentially receive and read μCAE devices having multiple microchannels.

Figure 8:
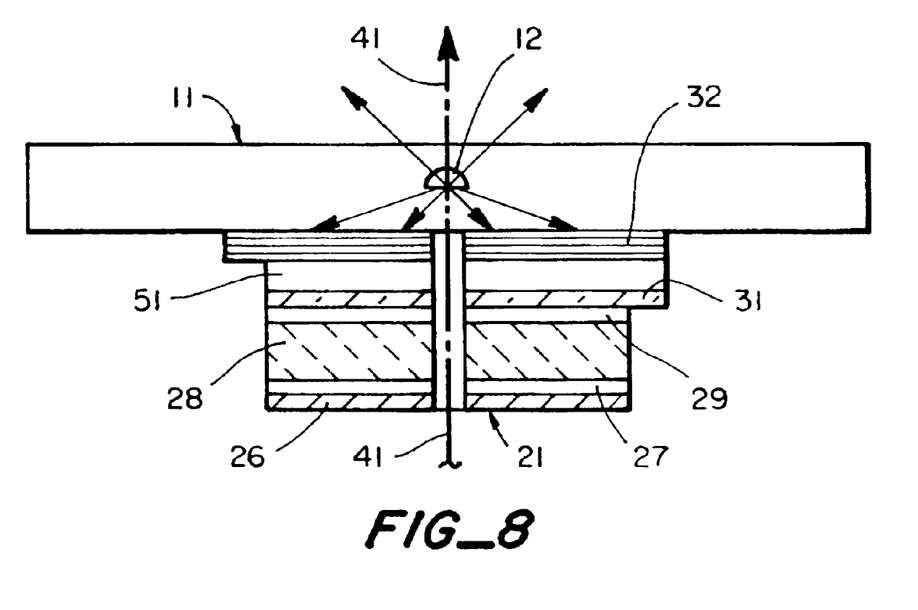
FIG. 8 shows an integrated filter and photodetector integrated with an electrophoresis device.
Figure 9:
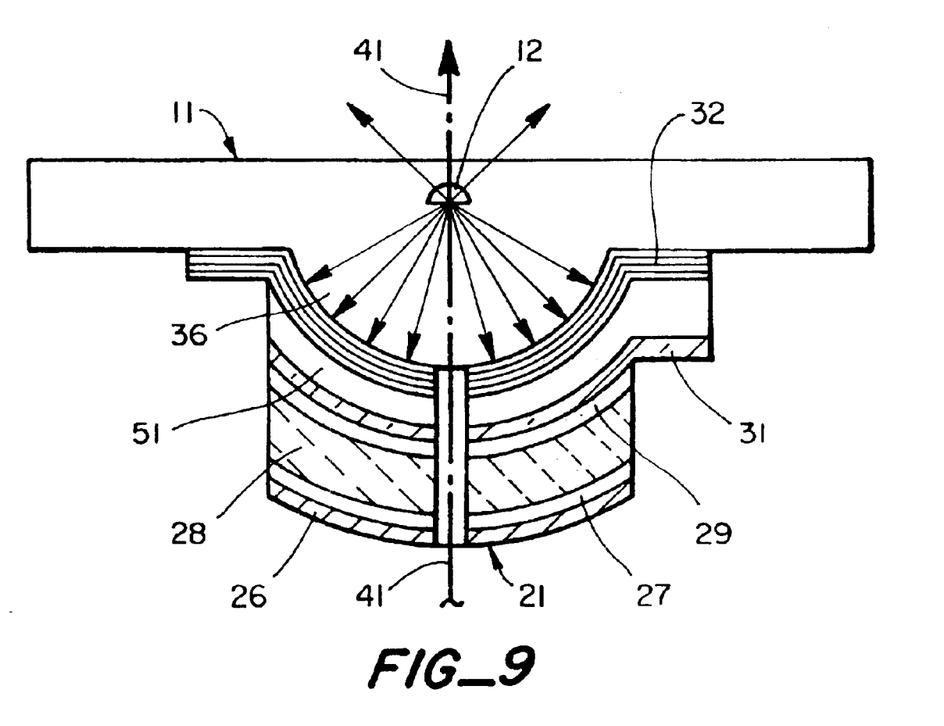
FIG. 9 shows the integrated device of FIG. 8 on a spherical surface.

FIGS. 8 and 9 present two examples of monolithic integration of the optical filter and a-Si:H detector on μCAE devices. Both structures require that the optical filter withstand a-Si:H deposition temperature of ~200° C. because the a-Si:H detector must be fabricated on the filter. A metal oxide multilayer interference filter such as SiO$_2$/TiO$_2$ can satisfy this condition because of their higher deposition temperature of 250–300° C. Thus, the optical filter is fabricated by depositing a multilayer interference filter 32 directly on the μCAE device 11 followed by the deposition of the a-Si:H layers of the photodiode 21 on a barrier layer 51. If such an interference filter is applied to the planar structure as shown in FIG. 8, the incident angle distribution of laser scattering light to the filter may be of concern. If the detector suffers from laser light scattering from various angles, edge absorption filters, or a combination of edge absorption filters and interference filters, could be used. In order to maintain planar structure and good light collimation, a planar graded refractive index lens (not shown) would be used on which an optical filter and an a-Si:H detector are monolithically integrated. It is also important to put the detector close enough to the CE channel to increase the efficiency of light gathering without the lens and to keep the diode detector smaller.

The other way to mitigate a wide-angle distribution of scattered light is to fabricate the filter on a spherical surface with a CE channel on center as shown in FIG. 9. Light from the CE channel enters normal to the filter surface. The curved detector could be detachable, as indicated by the dashed line in FIG. 9. In this case, index-matching fluid might be applied between the lens 36 and the μCAE device 11. A combination of edge absorption filter and interference filter would be a plausible choice as well. If the optical filters contain harmful elements for an a-Si:H detector, a barrier layer 51 such as silicon oxide or silicon nitride might be applied to prevent their diffusion into the detector. In order for the detector to be isolated from the high electric field, this diffusion barrier layer could be replaced with grounded transparent conductive oxide (TCO) such as ITO, SnO$_2$, or Al or Ga doped ZnO.

An a-Si:H PIN photodiode has been shown to operate very well even on a curved surface, and film conformity is also good mainly due to high deposition pressure of plasma enhanced chemical vapor deposition (CVD). Similarly, a uniform film thickness might be accomplished in the optical filter on a curved surface by using a higher working pressure process such as CVD and sputtering. Spray coating could be used rather than conventional spin coating to cover the curved surface with photoresist, and conventional wafer exposure such as contact and proximity printing could transfer mask pattern on the photoresist. The pinhole on the top curved surface can be close enough to the mask that pattern transfer would be acceptable. On the other hand, the outer edges of the detector and optical filter are far away (a few mm) from the mask, so that the resolution of the mask pattern is degraded due to the diffraction effects. In this case, however, it would not be a problem, thanks to the large feature size of the devices (a few mm).

Figure 10:
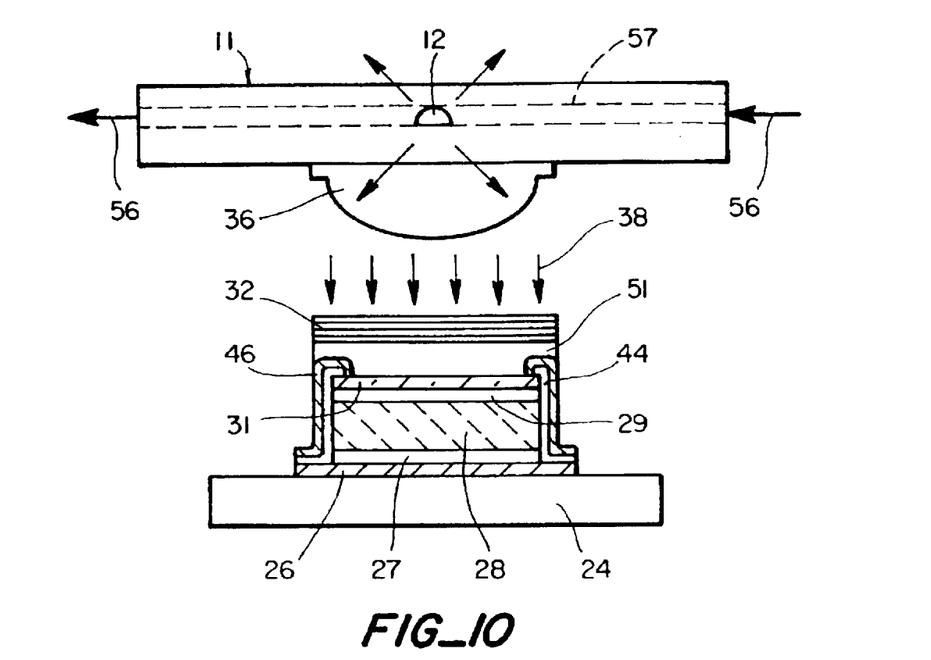
FIG. 10 shows a system in which the excitation light is applied parallel to the plane of the electrophoresis device.
Figure 11:
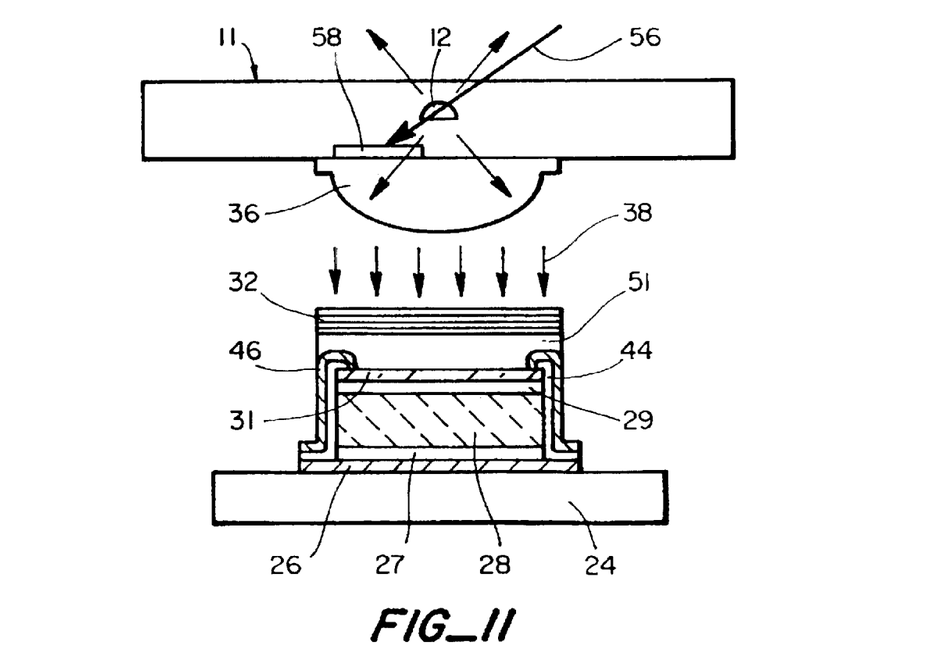
FIG. 11 shows a system in which the excitation light is applied at an angle with respect to the plane of the electrophoresis device.

FIGS. 10 and 11 show alternative ways to introduce laser light into the channels of μCAE devices. In FIG. 10, channels 12 are irradiated by laser light 56 parallel to the plane of the μCAE device which can be done directly through the μCAE substrate or might utilize an intrinsic waveguide 57. Thin, high-refractive index material can be deposited on or in the glass substrate as a waveguide intersecting the CE channel 12. The in-plane laser excitation avoids direct entrance of laser light into the filter 32 and detector unit 21 without the use of a pinhole. Off-axis angle laser excitation, especially Brewster angle excitation, could also be used to do this as shown in FIG. 11. A beam block 58 might be used to prevent laser light from entering the filter 32 and detector unit 21. Alternatively, the laser beam 56 can be introduced from the bottom with a mirror or prism directing the beam through the channel.

Figure 12:
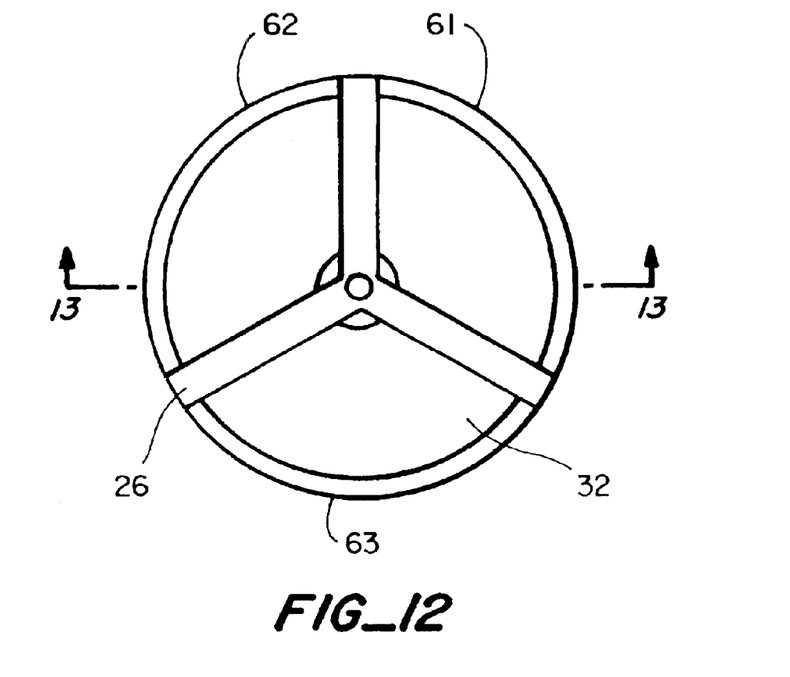
FIG. 12 shows a filter/detector which is partitioned to detect light of multiple wavelengths.
Figure 13:
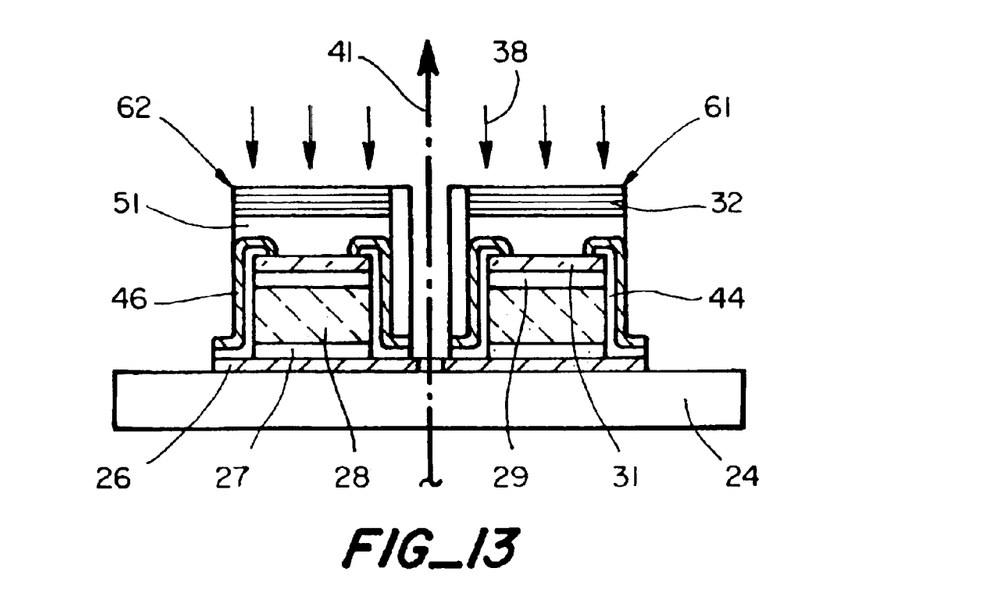
FIG. 13 is a sectional view taken along the line 13—13 of FIG. 12.

If the detector is sectored into two or more parts with similar partitioning of the optical filter for different wavelength, multi-color detection could be possible as well, although light intensity per sectored detector is reduced. The a-Si:H detector can be replaced with more sensitive detectors such as micro-PMT, avalanche photodiode (APD), or APD array, whether or not it is a crystalline or amorphous semiconductor. Referring to FIGS. 12 and 13, a partitioned filter/detector assembly is shown. The filter/detector includes three filter/detectors 61, 62 and 63. Each of the filter/detectors are fabricated as previously described and like reference numbers have been applied to like parts.

Figure 14:
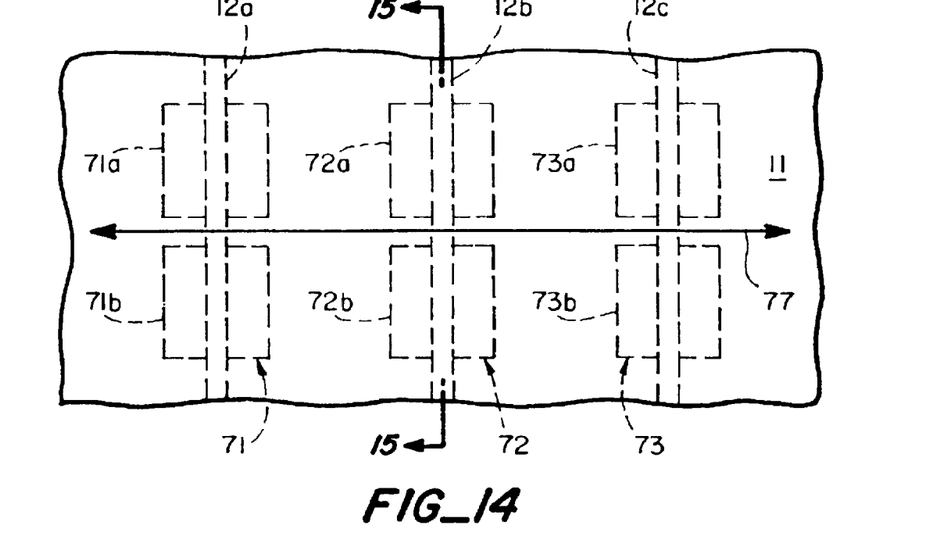
FIG. 14 is a schematic view of another detector array.
Figure 15:
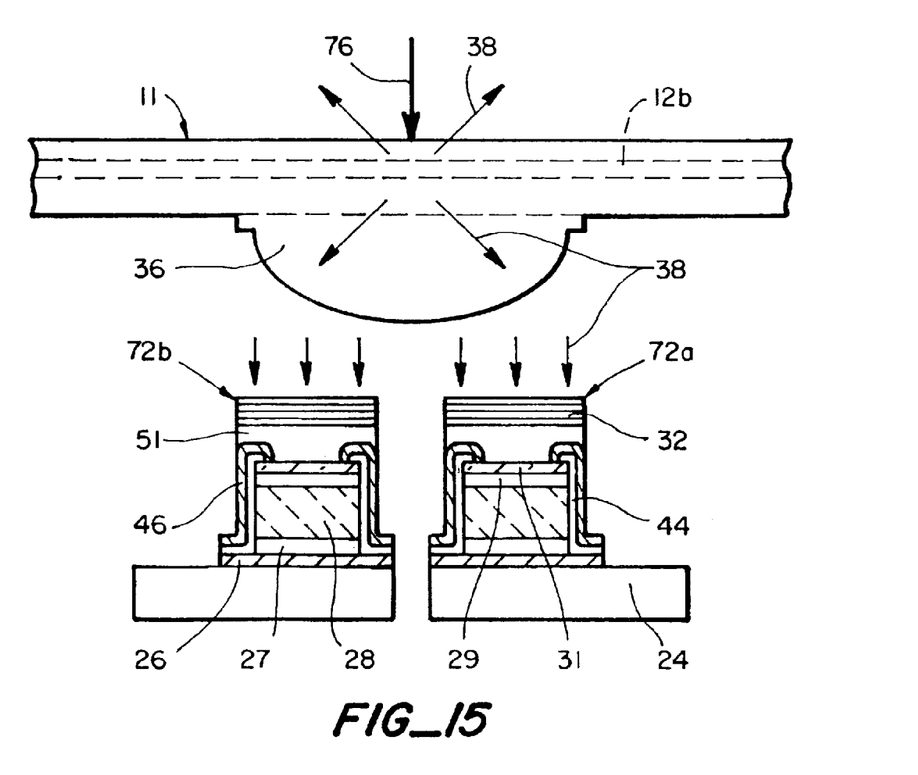
FIG. 15 is a sectional view taken along the line 15—15 of FIG. 14.

The detector can be sectioned in other configurations. Referring to FIGS. 14 and 15, the detectors 71, 72 and 73 are each partitioned into two sections 71a, 71b, 72a, 72b, and 73a, 73b. The two sections are disposed along the capillary channels 12a, 12b and 12c formed in a μCAE device 11 having a plurality of channels, only three of which are shown. Each detector includes a photodetector and filter with the filters in adjacent detectors passing emitted light of a different wavelength to the adjacent detectors. The detectors are fabricated as previously described, and therefore have like reference numerals. A lens 36 is associated with each pair. The excitation light beam 76 is scanned along the line 77. It is apparent that other configurations of multiple integrated multicolor detectors are within the teaching of the present invention.

In the present invention, the use of a-Si:H photodiode is emphasized for the integrated detector. However, it should be pointed out here that other glass-compatible semiconductors such as hydrogenated microcrystalline Si (μc-Si:H) or low-temperature grown poly-Si are also feasible as the material for the integrated detector. μc-Si:H is made by the same method as a-Si:H but under different conditions, while poly Si is grown by plasma-enhanced CVD, low pressure CVD or atmospheric pressure CVD, combined with laser or metal-induced crystallization of amorphous Si films. Even though they show much higher dark conductivities than a-Si:H, these forms of Si show higher sensitivity in red or infrared region, so that they might be more suited to detect red fluorescence. The sensitivity of a-Si:H in the red light region can be enhanced by incorporating Ge into a-Si:H, which is a-SiGe:H.

The a-Si:H integrated sensor optical system described here would be useful in all types of microfabricated electrophoretic protein and DNA assays including arrays based on fluorescence detection (M. Schena ed., "Microarray Biochip Technology," Eaton Pub. Co., 1$^{st}$ Ed. (2000)). Such electrophoretic devices include those that perform capillary electrophoresis, free zone electrophoresis and isoelectric focusing. Possible applications include DNA fragment sizing, DNA sequencing, DNA pyrosequencing, polymorphism analysis, protein separation, amino acid analysis, and cell sorting, pathogen and infectious disease detection, and food and water purity tests. In particular, the fluorescence-based devices that perform massively multiplexed assays will benefit from integrated a-Si:H sensor systems coupled with VCSEL technology with an ease of manufacturing and a reduction of product costs.

What is claimed:

1. A detector system for detecting light emitted at a first wavelength by fluorophores responsive to excitation light at a second wavelength comprising:

an integrated photodetector opposite said fluorophores, an optical filter between said fluorophores and said integrated photodetector configured to reject light at the second wavelength and pass light emitted at the first wavelength to the photodetector, and an aperture in said integrated photodetector and optical filter through which the excitation light projects to impinge upon the fluorophores.

2. A detector system as in claim 1 in which the photodetector is an a-Si:H photodiode.

3. A detector system as in claim 1 or 2 including a lens between the fluorophores and the optical filter for collimating the emitted light and directing it to the optical filter.

4. A detector system as in claim 3 in which the filter is integrated with the photodetector.

5. A detector system as in claim 4 in which the lens is selected from the group comprising convex lens, aspheric, half-ball, graded refractive index or diffractive.

6. A detector system as in claim 1 or 2 in which the filter and photodetector are partitioned and each partition of the filter passes light at a different wavelength than the other partition of the filter and each partition of the integrated photodetector detects the light passed by its respective filter partition.

7. A detector system as in claim 6 including a lens for collimating the emitted light and directing it to the partitioned filter and photodetector.

8. A detector system as in claim 7 in which the lens is integrated with the integrated photodetector and optical filter.

9. A detector system as in claim 1 or 2 including a VCSEL opposite said integrated photodetector aperture for generating and projecting light through said aperture.

10. A detector system for detecting analyte which has been tagged with fluorophores which fluoresce and emit light of predetermined wavelengths comprising:

an apertured integrated photodetector and an optical filter configured to pass light at said predetermined wavelength to said photodetector, a collimating lens for gathering and directing the emitted light onto said integrated photodetector and optical filter, and a laser for directing a light beam of different wavelength onto said tagged analyte to cause emission of light at said predetermined wavelength.

11. A detector system as in claim 10 in which the photodetector and filter includes an aperture through which the light beam is projected.

12. A detector system as in claim 11 in which the laser comprises a VCSEL.

13. A detector system as in claim 10, 11 or 12 in which the photodetector is an a-Si:H photodiode.

14. A detector system as in claim 11 in which the VCSEL is integrated with the integrated photodetector and filter.

15. A detector system as in claim 14 in which the photodetector is an a-Si:H photodiode.

16. A detector system for detecting light emitted by fluorophores at a plurality of spaced locations comprising:

an integrated system including a plurality of apertured photodetectors and optical filters each disposed to detect emitted light at a corresponding one of said spaced locations and a plurality of lasers for projecting light through said aperture to an associated fluorophore to cause emission of light.

17. A detector system as in claim 16 in which each of said photodetectors and optical filters is partitioned and each partition receives light emitted by the fluorophore located at the corresponding location.

18. A detector system as in claim 17 in which a lens is associated with each of said partitioned photodetectors and filters to direct light to the partitioned filters.

19. A detector system as in claims 16, or 17 in which the plurality of photodetectors and filters is arranged in a one-dimensional array.

20. A detector system as in claims 16 or 17 in which the plurality of photodetectors and filters is arranged in a two-dimensional array.

21. A detector system for detecting light emitted by fluorophores in analytes at a plurality of spaced locations at corresponding first wavelengths responsive to excitation light of a second wavelength, comprising:

a plurality of integrated photodetectors, one for each of said spaced locations and located opposite said locations, a plurality of optical filters, one for each of said integrated photodetectors, disposed between said locations, said integrated detectors configured to reject light at the second wavelength and pass light emitted at the first wavelengths to the integrated photodetectors, an aperture formed in each of said integrated detectors and optical filters through which the excitation light projects to impinge upon the fluorophores at each of said plurality of locations, and a lens at each of said locations for collimating the emitted light and directing it to the optical filter.

22. A detector system as in claim 21 in which the photodetector is an a-Si:H photodiode.

23. A detector system as in claim 21 in which the lens is integrated with the monolithic photodetector and filter.

24. A detector system as in claim 21 in which the lens is selected from the group comprising convex lens, aspheric, half-ball, graded refractive index or diffractive.

25. A detector system as in claim 21 in which the filter and photodetector are partitioned and each partitioned filter passes light at a different wavelength than the other partitioned filters, whereby to detect light emitted by the fluorophores at different wavelengths.

26. In an electrophoresis system having a microfabricated capillary array, a solid-state detector system for detecting light emitted by fluorophores in analyte in each of said capillary channels at corresponding first wavelengths responsive to excitation light at a second wavelength, comprising:

a plurality of integrated photodetectors, one for each of said spaced locations and located opposite said locations, a plurality of optical filters, one for each of said integrated photodetectors, disposed between said locations and said integrated detectors, said optical filters configured to reject light at the second wavelength and pass light emitted at the first wavelengths to the integrated photodetectors, and an aperture formed in each of said integrated detectors and optical filters through which the excitation light projects to impinge upon the fluorophores at each of said plurality of locations.

27. An electrophoresis system as in claim 26 in which the lens is integrated with the monolithic photodetector and filter.

28. An electrophoresis system as in claim 26 in which the filter and photodetector are partitioned and each partitioned filter passes light at a different wavelength than the other partitioned filters, whereby to detect light emitted by the fluorophores at different wavelengths.

29. An electrophoresis system as in claim 26 or 28 including a light blocking filter in said aperture to prevent excitation light from impinging on said integrated photodetectors.

* * * * *